United States Patent [19]
Anthony

[11] Patent Number: 6,029,670
[45] Date of Patent: Feb. 29, 2000

[54] HELMET ASSISTED CANALITH REPOSITIONING MANEUVER

[76] Inventor: Philip F. Anthony, 6601 Pine Valley Pl., Fort Worth, Tex. 76132

[21] Appl. No.: 09/143,719

[22] Filed: Aug. 31, 1998

[51] Int. Cl.$^7$ .................................................. A61B 19/00
[52] U.S. Cl. ............................................................ 128/897
[58] Field of Search .................................. 600/300, 301; 128/897, 898

[56] References Cited

U.S. PATENT DOCUMENTS

| | | |
|---|---|---|
| 4,466,438 | 8/1984 | Katz . |
| 4,576,184 | 3/1986 | Westerman .............................. 600/546 |
| 4,984,579 | 1/1991 | Burgert et al. . |
| 5,561,866 | 10/1996 | Ross . |
| 5,849,008 | 12/1998 | Anthony .................................... 606/15 |

*Primary Examiner*—Samuel Gilbert
*Attorney, Agent, or Firm*—Arthur F Zobal

[57] ABSTRACT

In one embodiment, the apparatus has two planar anterior surfaces, and two posterior planar surfaces located such that the two anterior surfaces are at the front of the apparatus and the two posterior surfaces are at the rear of the apparatus. Opposite anterior and posterior surfaces flare outward and downward relative to each other at angles of about 20 degrees. As seen from an upper plan view of the apparatus, adjacent surfaces form an angle of 90 degrees. A cavity is formed in the apparatus from the lower end for receiving a person's head with the anterior surfaces being located at the front of the person's head and the posterior surfaces being located at the rear of the person's head. In using the apparatus, the patients head is vibrated and the patient wearing the apparatus lies on the floor with the apparatus on and sequentially places the posterior right, posterior left, and anterior left planar surfaces against the floor or the posterior left, posterior right, and anterior right planar surfaces against the floor depending on which ear is effected.

17 Claims, 7 Drawing Sheets

HELMET ASSISTED CANALITH REPOSITIONING MANEUVER

BACKGROUND OF THE INVENTION

1. Field of the Invention

The invention relates to an apparatus and the use thereof to assist in the Canalith Repositioning Maneuver.

2. Description of the Prior Art

Approximately 3 million of the 250 million people in the United States suffer from vertigo of some duration each year. Vertigo is the most common physician visit diagnosis in patients over 65 years of age. 17% of patients who have vertigo have benign paroxysmal positional vertigo. Positional vertigo is characterized by vertigo when the patient moves into the effected ear downward position. The patient may also have symptoms of vertigo with looking up or looking down. The diagnosis is clinically confirmed by placing the patient in the effected ear down position and observing a characteristic rotary jerking motion of the eyes. The natural history of positional vertigo is one of spontaneous remission. Recurrence is common and can last for weeks to months. One ear is usually involved but reports of 15% of bilateral ear involvement have been made.

Positional vertigo is caused by dislodgment of naturally occurring inner ear calcium carbonate crystals (121, FIG. 1). When these crystals fall from their normal position in the inner ear (the utricular macula (123), two events that effect one of the inner ear sensors (the posterior semi-circular canal) can occur. (1.) When the patient places the effected ear downward, the loosened crystal (121-L) causes motion of the rotation sensor (127), causing the patient to sense vertigo. (2.) When the patient places the effected ear downward, the loosened crystals (121-B) move together within the membranous semicircular canal (141), and their aggregate effect is to cause motion of the endolymphatic fluid (95). The motion of that fluid and the motion of that fluid in a narrow channel (141), the membranous semicircular canal of small cross sectional diameter, has a significant effect on the much broader surfaced area (127) rotation sensor, causing the patient to sense vertigo.

In those patients whom multiple loosened crystals (121-B) have collected in the posterior semi-circular canal, a treatment is available.

The presence of loosened crystals (121-B) was identified and their effect on the rotation sensor (127) is explained by John Epley, M.D., approximately eight years ago. Dr. Epley hypothesized and then demonstrated that by rotating the patient's head in the plane of the effected inner ear rotation sensor (the posterior semicircular canal, 131), the loosened crystals (121-B) can be caused to fall through the fluid of the posterior membranous semi-circular canal 141 away from the rotation sensor (127) and fall into the large compartment of the endolymphatic fluid compartment (93) (128) the utricle. In this position crystals delivered by this head rotation maneuver into the utricular portion of the endolymphatic space cause fewer symptoms and presumably dissolve more rapidly than in the membranous posterior semi-circular canal much smaller fluid space (141).

The technique that Dr. Epley described has been reported by multiple authors and is thought to be a good and valid technique.

The performance of this Canalith repositioning maneuver (Eply maneuver) by other physicians or paramedical personnel is difficult to teach. Inconsistent performance and performing this maneuver in an incorrect method is a continuing problem. Consistent performance of this maneuver by the apparatus of the invention allows a method to help paramedical personnel consistently perform the Epley maneuver or allows the patient to perform the maneuver consistently without supervision.

The literature reports that the use of a head vibrator for some period of time prior to performance of an Canalith repositioning maneuver increases the efficiency of the movement of the loosened crystals (121-B) from the posterior semi-circular canal membranous labyrinth into the utricle. A vibrator can be attached to the apparatus of the invention. The vibrator may be attached internally or externally to the apparatus.

SUMMARY OF THE INVENTION

It is an object of the invention to provide an apparatus to be worn on the head of a human to act as a guide to allow one to obtain consistent performance of the Canalith Repositioning Maneuver by the medical personnel or by the patient without medical attention when the diagnosis is clear. The apparatus also allows the patient to treat medically diagnosed benign paroxysmal positional vertigo when the episodes are recurrent. The technique does not require return of the patient to a medical facility or medical personnel.

In one embodiment, the apparatus comprises two planar anterior surfaces and two posterior planar surfaces located such that the two anterior surfaces are at the front of the apparatus and the two posterior surfaces are at the rear of the apparatus. Opposite anterior and posterior surfaces flare outward and downward relative to each other. A cavity is formed in the apparatus from the lower end. This apparatus may be used to treat either ear.

In one embodiment, each surface forms an angle of about 20 degrees relative to a central axis extending between the upper and lower ends of the apparatus and as seen from a top plan view, the adjacent surfaces define an angle of about 90 degrees.

In another embodiment, the apparatus may comprise the two posterior surfaces and only one of the anterior surfaces such that separate apparatuses are employed to treat either ear.

In a further aspect, a vibrator may be attached to the apparatus.

Initially the patient's head may be vibrated with a vibrator. If the right ear is effected, the patient lays on his or her back with the right posterior surface against a support surface, then with the left posterior surface against the support surface and then rolls over to allow the left anterior surface to be placed against the support surface. If the left ear is effected, the patient lays on his or her back with the left posterior surface against the support surface, then with the right posterior surface against the support surface and then rolls over to allow the right anterior surface to be placed against the support surface.

BRIEF DESCRIPTION OF THE DRAWINGS

FIG. 17 is a right side view of the apparatus.

FIG. 18 is a left side view of the apparatus.

FIG. 19 is a front view of the apparatus.

FIG. 20 is a top plan view of the apparatus.

FIG. 21 is a cross-section outline of FIG. 20 taken along the lines 21—21 thereof.

FIG. 22 is a cross-section outline of FIG. 20 taken along the lines 22—22 thereof.

DESCRIPTION OF THE PREFERRED EMBODIMENTS

Figure 1:
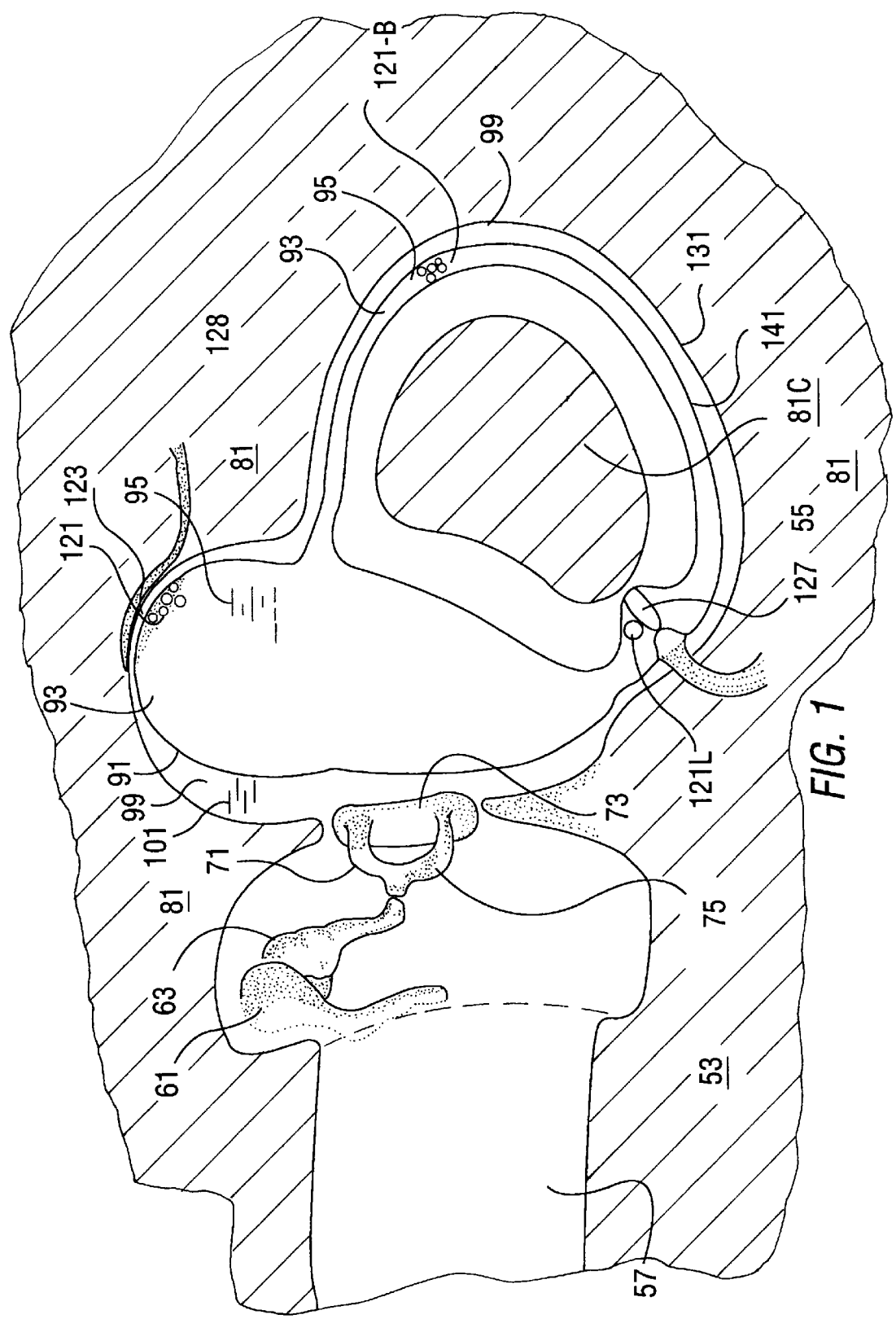
FIG. 1 illustrates the middle and inner ear of a human.

In order to complete the previous description of the human ear, the external ear canal, middle, and inner ear of a human are identified by reference numerals 57, 53, and 55 respectively in FIG. 1. Members 61 and 63 are the malleus and incus respectfully. Members 71, 73, 75 are the stapes bone. The cross hatching 81 indicates bone. Member 91 is a transparent membrane which forms and defines a endolymphatic fluid compartment 93 containing transparent endolymphatic fluid 95. The fluid compartment 93 also extends around the center bone structure 81C. The space 99 between the membrane 91 and the outer bone structure 81 is a fluid compartment containing transparent perilymphatic fluid 101.

Referring now to FIGS. 2–7 the apparatus of the invention is identified by reference numeral 221. It comprises four outer walls 223, 225, 227 and 229 having flat outer surfaces or planes each in the form of a trapezoid with each trapezoid having parallel upper and lower edges of different lengths and two side edges of equal lengths. The side edges of the walls 223, 225, 227 and 229 are joined to form four corners 231, 233, 235, 337. Each of the surfaces 223, 225, 227, 229 are identical in shape and dimension. The lower edges of the walls 223, 225, 227, 229 define a square bottom 241 in a lower plane and the upper edges of the walls 223, 225, 227, 229 define square top 243 in an upper plane parallel to the plane of the bottom 241. As seen in a top plan view of the apparatus in FIG. 4, the surfaces of each of the surface pairs 223, 225; 225, 227; 227, 229; and 229, 231 are at about 90 degrees relative to each other such that each of the angles β is equal to about 45 degrees. The corners 231 and 235 define a plane which bisects the apparatus and the corners 233 and 237 define a plane which bisects the apparatus.

Figure 5:
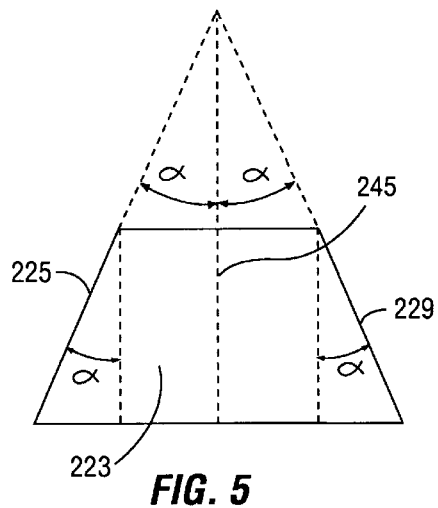
FIG. 5 is a side view of the apparatus of the invention as seen from the front left side.
Figure 6:
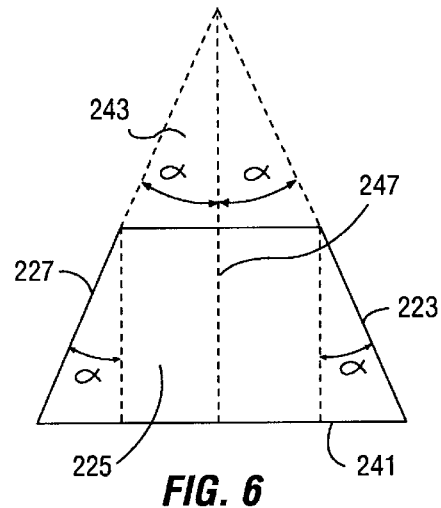
FIG. 6 is a side view of the apparatus of the invention as seen from the front right side.
Figure 4:
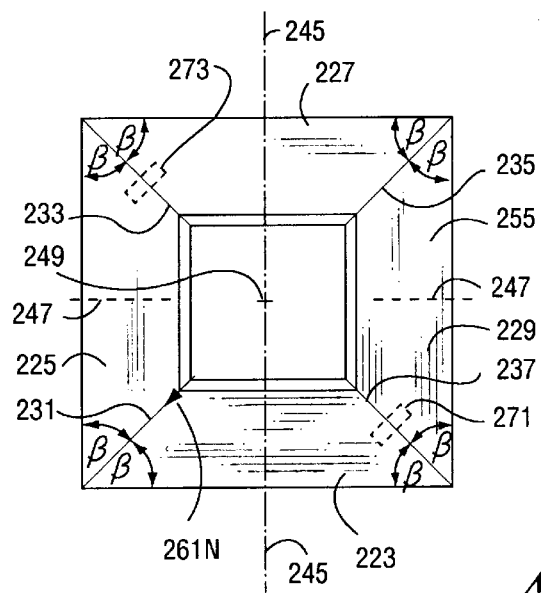
FIG. 4 is a top view of the apparatus of the invention.

Each of the angles α between the plane 245 and the surfaces 225 and 229 is equal to about 20 degrees and the angles α between the plane 247 and the surfaces 223 and 227 is equal to about 20 degrees. In FIGS. 5 and 6 each of the lower angles α is equal to about 20 degrees. In FIG. 4, reference numeral 249 defines a central axis passing through the lower and upper ends of the walls 223, 225, 227, and 229.

The inside of the apparatus 221 has an inner helmet 251 connected to the outer walls 223, 225, 227, and 229 by way of plastic material 253 which may be a suitable plastic foam. The inner helmet has a cavity 255 with a lower opening 257 for receiving a person's head shown at 261. The inner helmet 251 is attached such that when a person wears the apparatus 221, corner 231 will be at the front of the person's head, corner 235 will be at the rear of the person's head and corners 237 and 233 will be on the left and right sides of the person's head as shown in FIGS. 2–4 and 7. In FIG. 4, the person's head is shown at 261 in dotted form with his or her nose indicated at 261N. In this position, the surface planes 223 and 225 are at the front left and front right of the person's head and the surface planes 229 and 227 are at the rear left and rear right of the person's head. The cavity 255 shaped as shown allows the helmet and apparatus to be worn on the head only in this manner.

Figure 16:
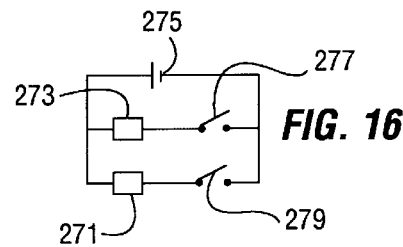
FIG. 16 is an electrical schematic of the circuitry for operating the vibrators.
Figure 7:
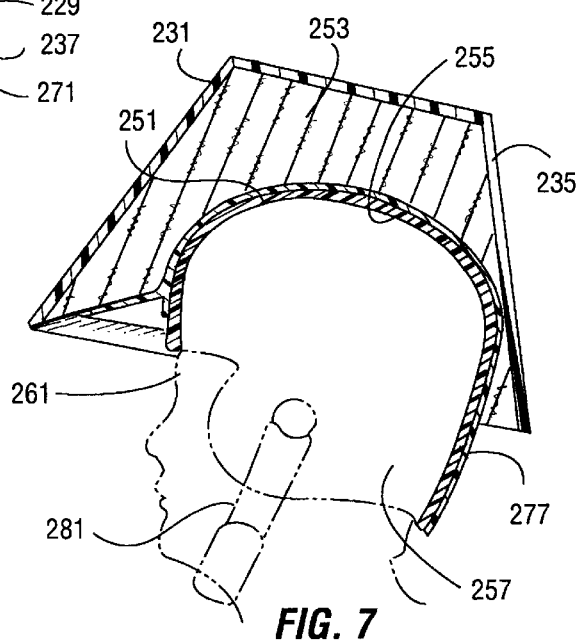
FIG. 7 is a cross sectional view of the apparatus of the invention as seen along lines 7—7 of FIG. 3.

Preferably two vibrators 271 and 273 are connected to the inner helmet 261 on each side of and in line with the ears as illustrated in FIGS. 4, 7, and 16. Preferably each of the vibrators will be operated by a battery 275 with an exterior switch 277 and 279.

Figure 2:
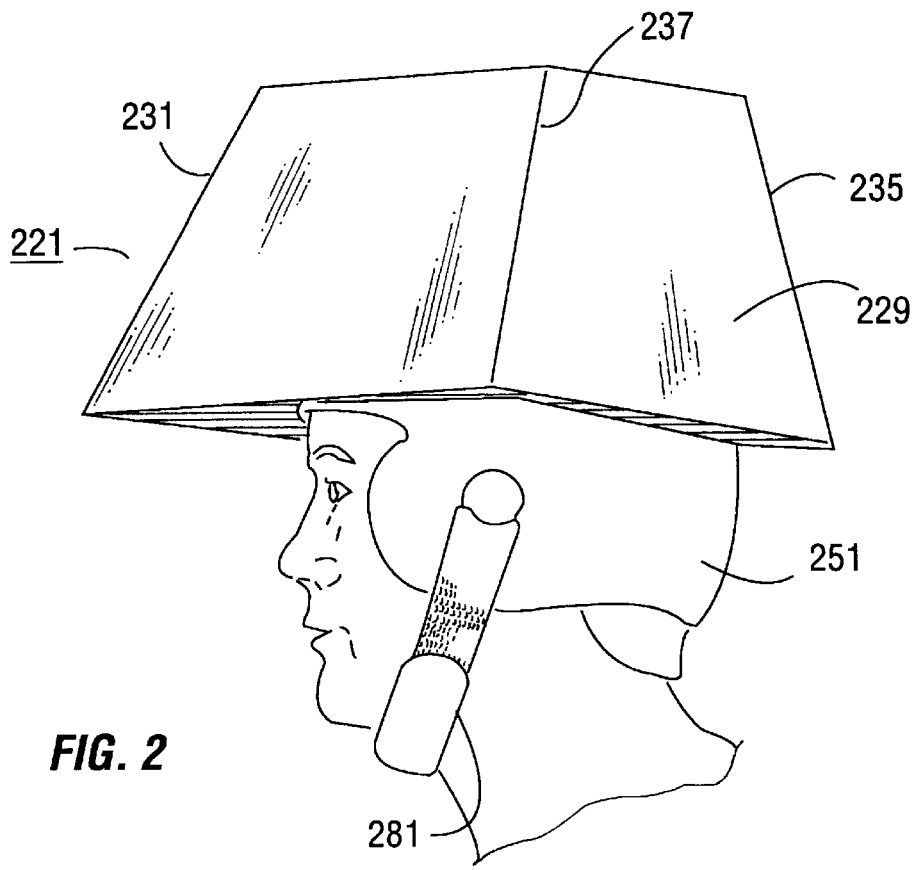
FIGS. 2 and 3 illustrate the apparatus of the invention on the head of a person as seen from the left side and the front side of the person.
Figure 3:
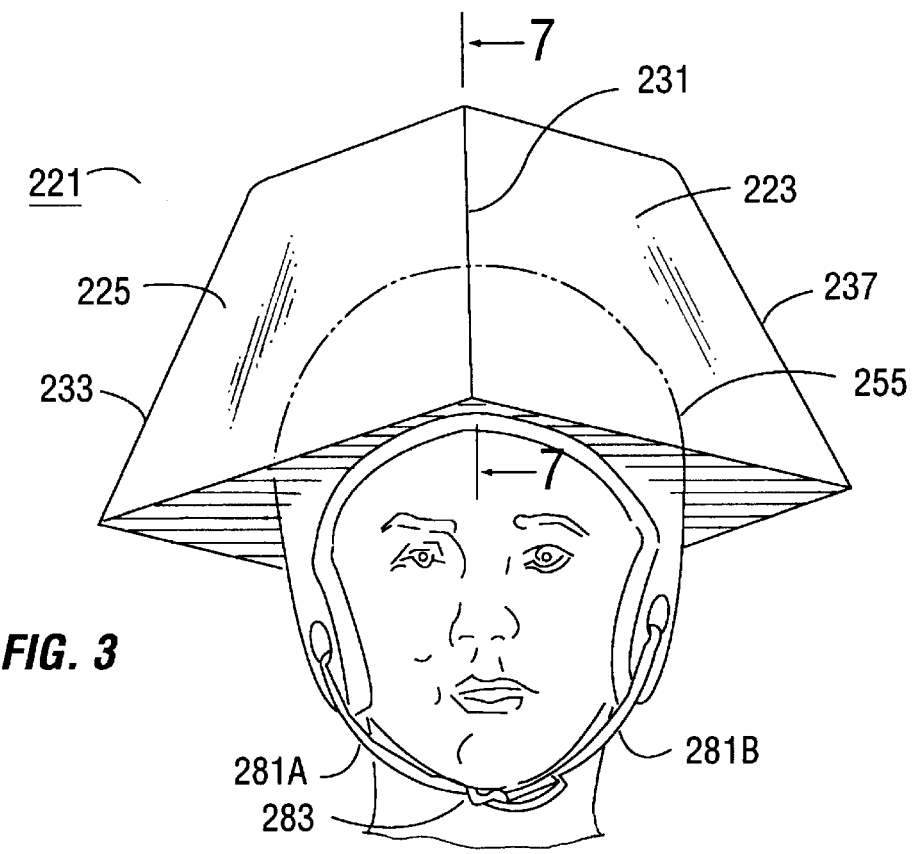

A chin strap 281 comprising strap members 281A and 281B is connected to each side of the inner helmet 251 such that the strap members may be located below the chin and connected together with the aide of a buckle 283 as shown in FIGS. 2, 3, and 7 to secure the apparatus 221 in place on the head of a person.

The positions in which the head is held are described with the wearer in the anatomic position, supine. The planes of the head are described as sagittal being a vertical plane running directly antero-posteriorly through the center of the skull; coronal plane, a vertical plane running supero-inferiorly and perfectly lateral to lateral; the horizontal plane, horizontal with the surface. The four planes 223, 225, 227, and 229 of the apparatus 221 are divided evenly between the right and the left sides of the skull. The two posterior planes 227 and 229 are equal to each other and the two anterior planes 223 and 225 are equal to each other.

While the wearer is lying in an anatomic position, supine, the posterior planes 227 and 229 of the helmet guide the wearer's head into positions: 1) twenty degrees of neck extension and forty-five degree head turn to the right; 2) twenty degrees of neck extension and forty-five degrees turn of the head to the left from the anatomic position. The front plane 225 of the apparatus with the patient lying in a full lateral position, holds the neck in a twenty degree flexed position with the head rotated forty-five degrees to the right. When the patient is in full left lateral position, the plane 223 of the helmet holds the head in a twenty degree flexed position and forty-five degree turn to the left from the anatomic position.

The process of helmet assisted Canalith repositioning maneuver is as follows. A determination is made as to the ear of origin of positional vertigo. This can be done by the patient having identified the ear, which when placed downward, will cause rotary nystagmus, and when placed upward will cease to cause nystagmus. The ear which in a downward position causes vertigo, is known to be the ear causing vertigo. The determination of positional vertigo can also be made by professional medical history and balance testing mechanisms and shared with the patient. If the helmet 221 does not have the vibrators 271 and 273, a vibrator is used to vibrate the head next to the effected ear. After the vibration of the head, the apparatus is placed on the patient and the chin strap 281 made firm. If the apparatus 221 has the vibrators 271 and 273, the apparatus 221 is placed on the patient's head and the chin strap 281 connected in place. The vibrator next to the effected ear is operated by closing its switch 277 or 279 for a period of time. With the vibrator running, the patient then is instructed to lie backward on a one inch thick mat 291 allowing his effected ear to hang off the mat, allowing the helmet to touch the floor 293. The entire surface of the back effected ear side surface plane is place flatly against the floor surface. After a 15 to 20 second pause, the patient should become vertiginous. This vertigo will last for some variable period of time (usually less than 90 seconds). As the vertigo decreases to only 10% of its maximum, the patient turns his or her head 90 degrees such that his non-effected ear is more downward than the effected ear. The entire surface of the back, non-effected ear, helmet plane is placed against the flat floor surface. The patient should expect some increase in dizziness 15 to 20 seconds after this maneuver. Again, when the symptoms have decreased to 10% of his or her non-effected ear downward plane vertigo, the patient can roll onto his or her non-effected ear side into a full lateral position. Following this, the patient rolls his or her head so that the non-effected ear front plane of the apparatus is flat against the floor. For the third time the patient should expect some increases in his or her dizziness. After 90% of the evoked dizziness in this position resolves (60 to 90 seconds), the patient sits up from his or her lateral position with his or her nose trailing. Immediately upon reaching a full upright position the chin is tipped downward for 10 seconds. One maneuver is now complete.

Figure 8:
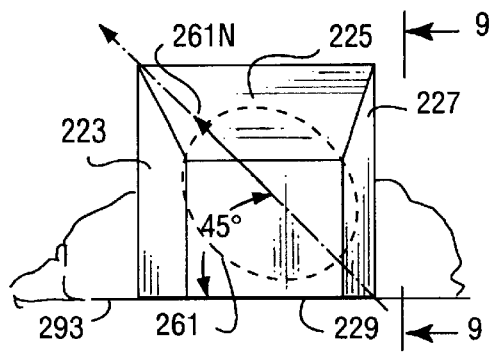
FIG. 8 is an end view of the apparatus of FIGS. 2–7 on the head of a person with the left rear side against the floor.
Figure 9:
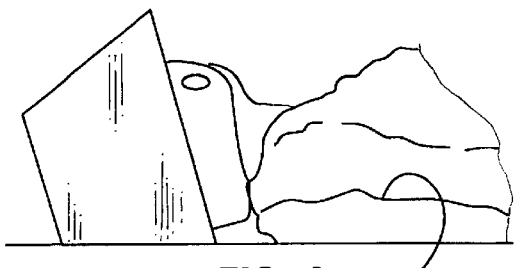
FIG. 9 is a view of FIG. 8 as seen along lines 9—9 thereof.
Figure 10:
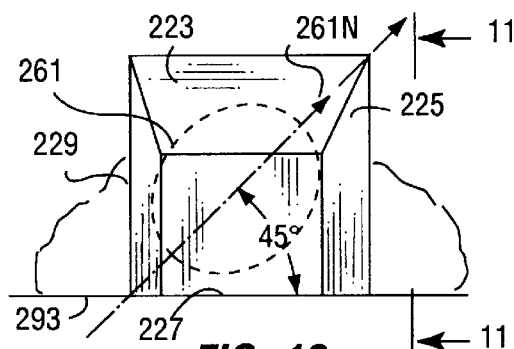
FIG. 10 is an end view of the apparatus of FIGS. 2–7 on the head of a person with the right rear side against the floor.
Figure 11:
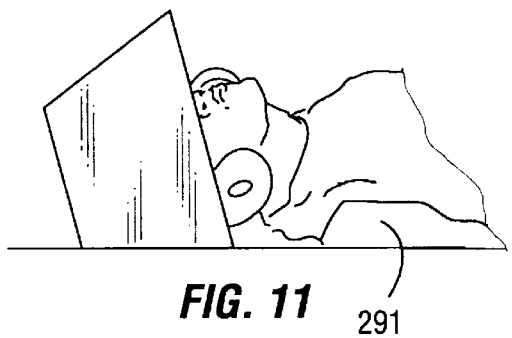
FIG. 11 is a view of FIG. 10 as seen along lines 11—11 thereof.
Figure 14:
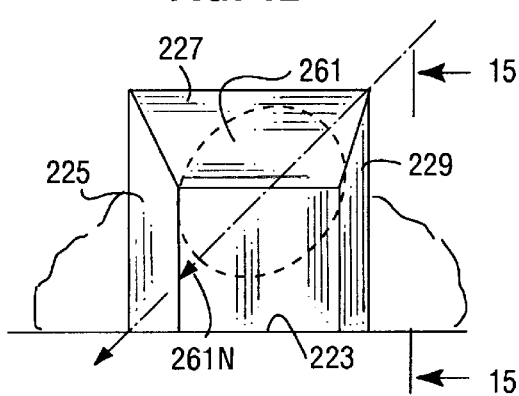
FIG. 14 is an end view of the apparatus of FIGS. 2–7 on the head of a person with the left front side against the floor.
Figure 15:
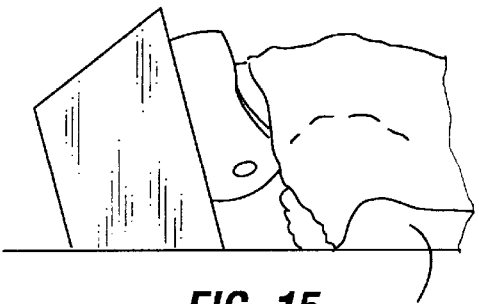
FIG. 15 is a view of FIG. 14 as seen along lines 15—15 thereof.
Figure 17:
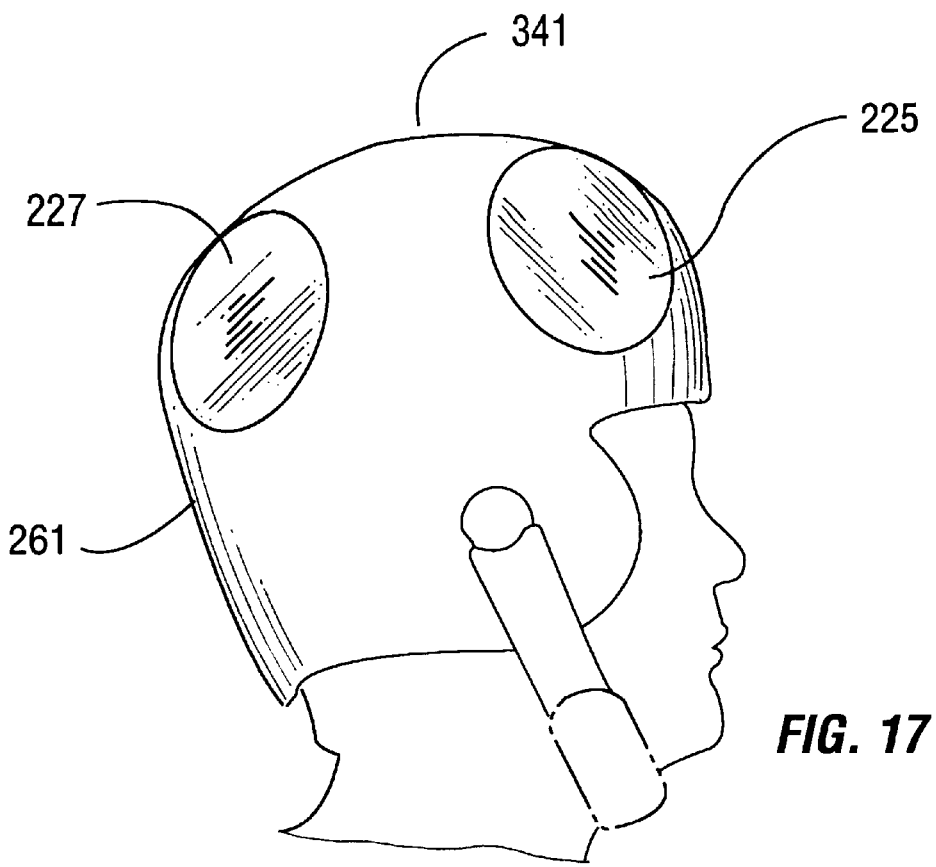
FIGS. 17–22 illustrates an integral guide and helmet of a second embodiment of the invention.
Figure 19:
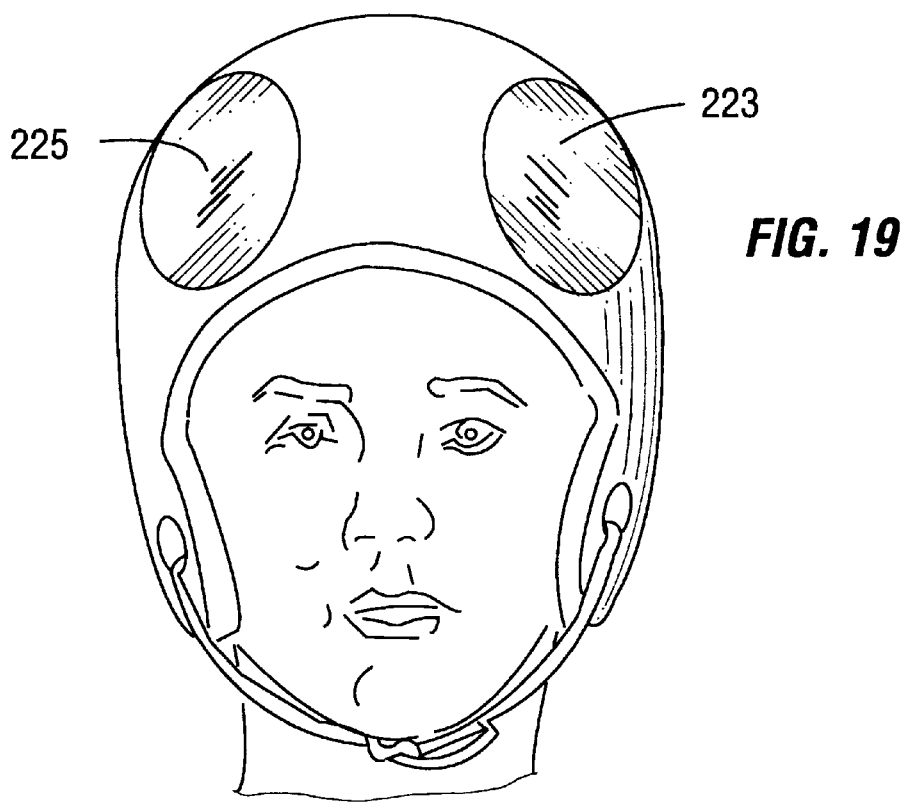
Figure 18:
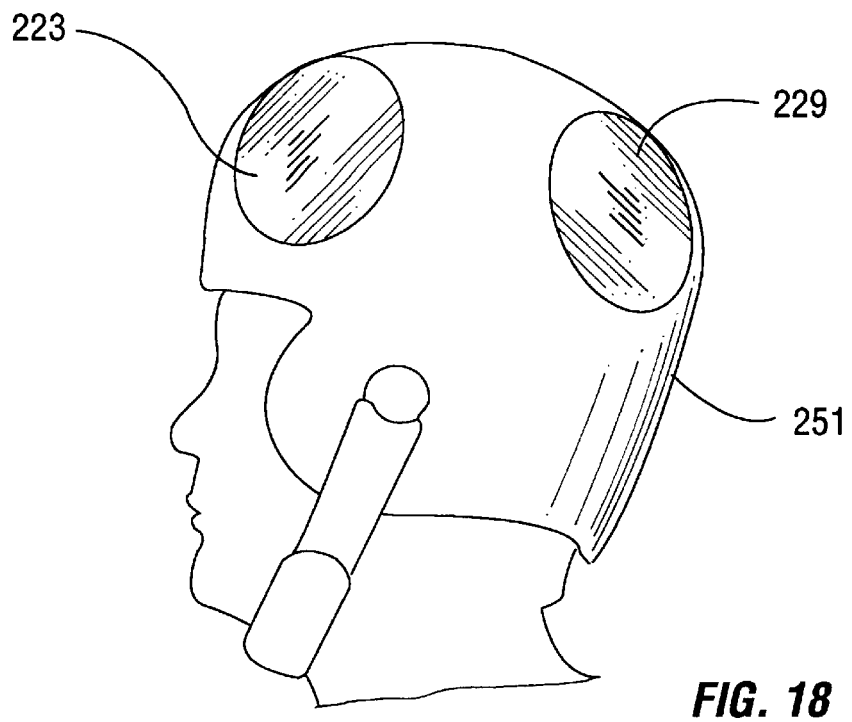
Figure 20:
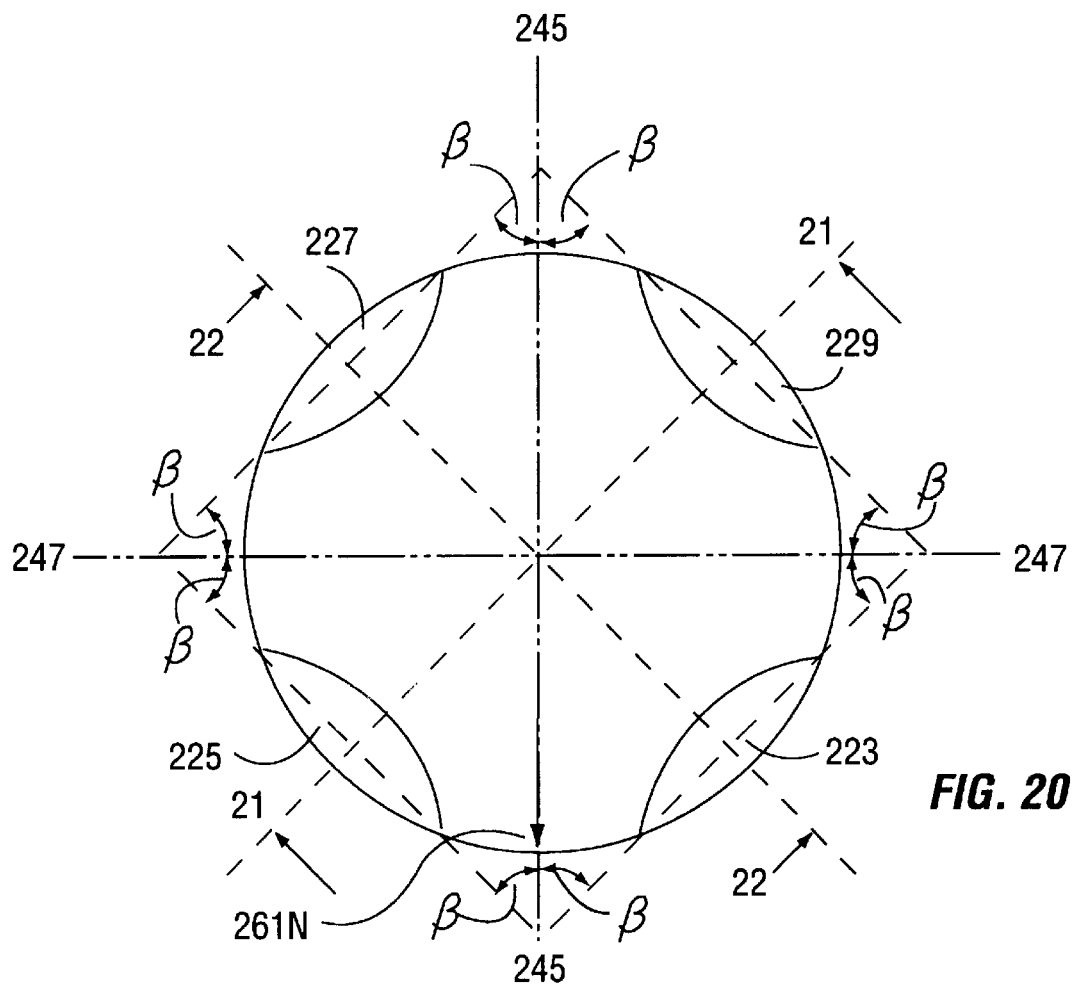
Figure 21:
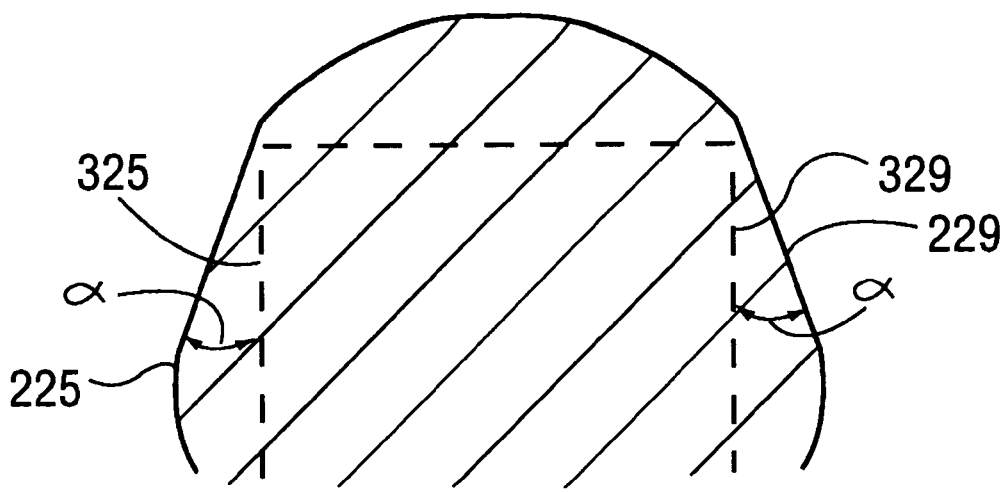
Figure 22:
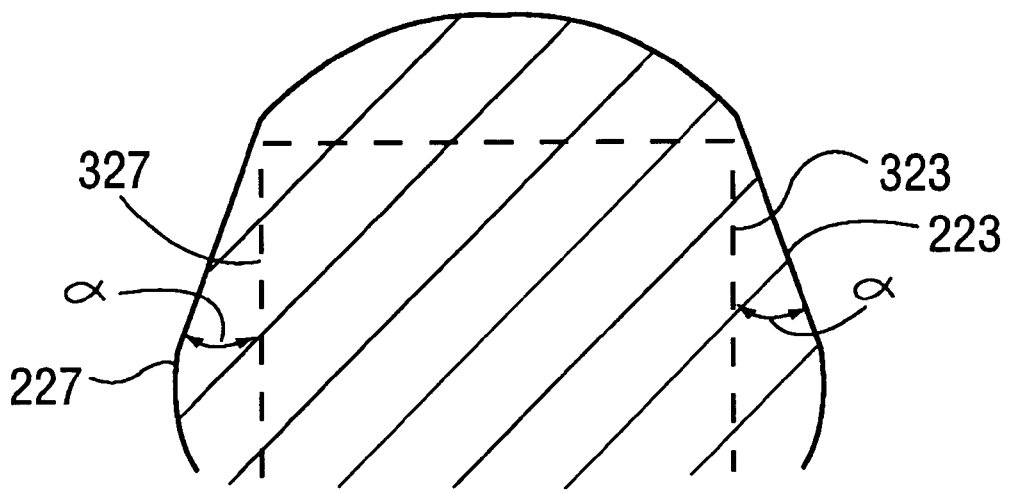

Referring to FIGS. 10, 11, 8, 9, and 14 15 assume that the patient's right ear is effected. With the apparatus 221 on the patient's head the patient lays with his or her back on the pad 291 with the surface plane 227 of the apparatus flat against the floor as shown in FIGS. 10 and 11. After a period of time as indicated above, the patient turns his or her head 90 degrees such that the surface plane 229 is flat against the floor 293 as shown in FIGS. 8 and 9. After a period of time as indicated above, the patient rolls over on his or her left full lateral (on left shoulder and hip) to place the surface plane 223 flat against the floor as shown in FIGS. 14 and 15, for a period of time and then the patient sits up as indicated above and the apparatus 221 then is removed.

Figure 12:
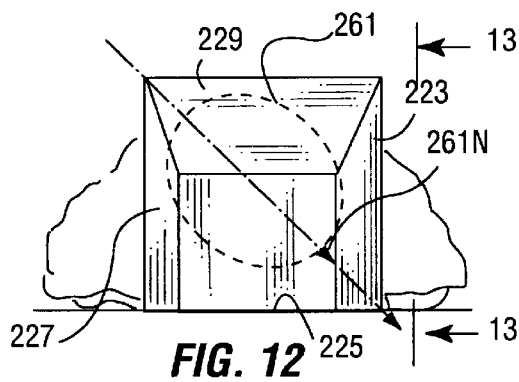
FIG. 12 is an end view of the apparatus of FIGS. 2–7 on the head of a person with the right front side against the floor.
Figure 13:
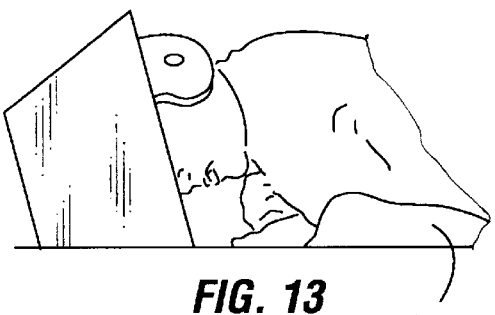
FIG. 13 is a view of FIG. 12 as seen along lines 13—13 thereof.

Referring to FIGS. 8, 9, 10, 11, 12, 13 assume that the patient's left ear is effected. With the apparatus 221 on the patient's head, the patient lays with his or her back on the pad 291 with the surface plane 229 of the apparatus flat against the floor 292 as shown in FIGS. 8 and 9. After a period of time as indicated above, the patient turns his or her head 90 degrees such that the surface plane 227 is flat against the floor 292 as shown in FIGS. 10 and 11. After a period of time, as indicated above, the patient rolls over on his or her full lateral (right should and hip) to place the surface plane 225 flat against the floor as shown in FIGS. 12 and 13, for a period of time and then the patient sits up as indicated above and the apparatus 221 then is removed.

In one embodiment, the inner helmet 251 and the helmet walls 223, 225, 227, and 229 may be formed of a suitable hard plastic material.

Referring to FIGS. 17–23, there is disclosed another embodiment wherein the planar surfaces 223, 225, 227, and 229 are integral with the helmet 251 which helmet is similar to the helmet 251 of the embodiment of FIGS. 2–16 except in a top plan view of the helmet, the helmet is circular as shown in FIG. 30. The planar surfaces 223, 225, 227, and 229 are circular in shape. Surfaces 223 and 227 form angles α equal to about 20 degrees relative to the vertical planes 323 and 327 and surfaces 225 and 229 form angles α equal to about 20 degrees relative to the vertical planes 325 and 329. Each of the angles β in planes parallel to the tops and bottoms of planar surfaces 223, 225, 227, and 229 is equal to about 45 degrees such that adjacent surfaces are about 90 degrees relative to each other. The helmet is worn such that the surfaces 223, 225, 227, and 229 are located in the positions shown in FIGS. 17–20.

The apparatus of FIGS. 17–23 is used in the same manner as the apparatus of the embodiment of FIGS. 2–16.

In the embodiments of FIGS. 2–16 and 17–22 it is understood that the apparatus may have only one front planar surface and two rear surfaces. For treating either the left or right ear, two of the apparatus will be employed. One apparatus will have the two rear surfaces 227 and 229 and only front surface 223 and the other apparatus will have the two rear surfaces 227 and 229 and only front surface 225.

I claim:

1. An apparatus to be worn by a person for use as a guide to allow placement of a person's head in different positions relative to a base surface for assisting in a canalith repositioning maneuver, said apparatus comprising:

a front end, a rear end, an upper end, and a lower end with a cavity formed in said apparatus from said lower end for receiving a person's head with the front of the person's head being located at said front end and the rear of the person's head being located at said rear end, a first pair of posterior and anterior, outer planar surfaces located on opposite sides of a first plane extending through said apparatus between said upper and lower ends, a second pair of posterior and anterior outer planar surfaces located on opposite sides of a second plane transverse to said first plane and extending through said apparatus between said upper and lower ends, each of said surfaces has an upper edge portion and a lower edge portion, said two surfaces of said first pair flare outward and downward relative to each other from their said upper edge portions, said two surfaces of said second pair flare outward and downward relative to each other from their said upper edge portions, said anterior surfaces of said first and second pairs have front edge portions respectively which are located near said front end of said apparatus near and on opposite sides of a central plane extending through said apparatus between said front and rear ends and between said upper and lower ends, said posterior surfaces of said first and second pair have rear edge portions respectively which are located near said rear end of said apparatus near and on opposite sides of said central plane.

2. The apparatus of claim 1, wherein:

each of said two surfaces of said first pair define an angle of about 20 degrees relative to said first plane, each of said two surfaces of said second pair define an angle of about 20 degrees relative to said second plane.

3. The apparatus of claim 2, wherein:

in a plan view of said apparatus as seen from said upper end thereof said anterior surfaces define an angle of about 90 degrees and said posterior surfaces define an angle of about 90 degrees.

4. The apparatus of claim 1, wherein:

in a plan view of said apparatus as seen from said upper end thereof said anterior surfaces define an angle of about 90 degrees and said posterior surfaces define an angle of about 90 degrees.

5. The apparatus of claim 1, comprising:

at least one electrically actuated vibrator coupled to said apparatus.

6. The apparatus of claim 1, wherein:

said anterior surfaces are coupled together at a front corner, said posterior surfaces are coupled together at a rear corner, one of said anterior surfaces of said first pair and one of said posterior surfaces of said second pair are coupled together at a side corner, the other of said anterior surfaces of said second pair and the other of said posterior surfaces of said first pair are coupled together at a side corner, wherein when said apparatus is worn by a person, said front corner is located at the front of the person's head, said rear corner is located at the rear of the person's head and said two side corners are located on the two sides of the person's head.

7. An apparatus to be worn by a person for use as a guide to allow placement of a person's head in different positions relative to a base surface for assisting in a canalith repositioning maneuver, said apparatus comprising:

a front end, a rear end, an upper end, and a lower end with a cavity formed in said apparatus from said lower end for receiving a person's head with the front of the person's head being located at said front end and the rear of the person's head being located at said rear end, said apparatus comprises a pair of posterior and anterior outer planar surfaces located on opposite sides of a first plane extending through said apparatus between said upper and lower ends and a second posterior surface located on one side, of a second plane transverse to said first plane and extending through said apparatus between said upper and lower ends, each of said surfaces has an upper edge portion and a lower edge portion, said surfaces of said pair of anterior and posterior surfaces flare outward and downward relative to each other from their said upper edge portions, said second posterior surface flares outward and downward relative to said second plane from its said upper edge portion, said posterior surfaces have rear edge portions respectively which are located near said rear end of said apparatus on opposite sides of a central plane extending through said apparatus between said front and rear ends and between said upper and lower ends, said anterior surface has a front edge portion which is located near said front end of said apparatus on one side of said central plane.

8. The apparatus of claim 7, wherein:

said rear edge portions of said posterior surfaces are coupled together at said rear end of said apparatus, said front edge portion of said anterior surface is located at said front end of said apparatus.

9. The apparatus of claim 7, comprising:

an electrically actuated vibrator coupled to said apparatus.

10. The apparatus of claim 7, wherein:

each of said surfaces of said pair of surface define and angle of about 20 degrees relative to said first plane, said second posterior surface defines an angle of about 20 degrees relative to said second plane.

11. The apparatus of claim 10, wherein:

in a plan view of said apparatus as seen from said upper end thereof, said posterior surfaces define an angle of about 90 degrees and said anterior surface and one of said posterior surfaces define angle of about 90 degrees.

12. The apparatus of claim 11, comprising:

at least one electrically actuated vibrator coupled to said apparatus.

13. The apparatus of claim 7, wherein:

in a plan view of said apparatus as seen from said upper end thereof, said posterior surfaces define an angle of about 90 degrees and said anterior surface and one of said posterior surfaces define angle of about 90 degrees.

14. A method of carrying out a Canalith repositioning maneuver with an apparatus of the type having a front end, a rear end, an upper end, and a lower end with a cavity formed in said apparatus from said lower end for receiving a person's head with the front of the person's head being located at said front end and the rear of the person's head being located at said rear end, a first pair of posterior and anterior, outer planar surfaces located on opposite sides of a first plane extending through said apparatus between said upper and lower ends, a second pair of posterior and anterior outer planar surfaces located on opposite sides of a second plane transverse to said first plane and extending through said apparatus between said upper and lower ends, each of said surfaces has an upper edge portion and a lower edge portion, said two surfaces of said first pair flare outward and downward relative to each other from their said upper edge portions, said two surfaces of said second pair flare outward and downward relative to each other from their said upper edge portions, said anterior surfaces of said first and second pairs have front edge portions respectively which are located near said front end of said apparatus near and on opposite sides of a central plane extending through said apparatus between said front and rear ends and between said upper and lower ends, said posterior surfaces of said first and second pair have rear edge portions respectively which are located near said rear end of said apparatus near and on opposite sides of said central plane comprising the steps of:

a) placing said apparatus on the head of person such that said front end and rear end are located at the front and rear of the person's head, b) with said apparatus on the head of the person, having the person lay down on his or her back, c) placing one of said posterior surfaces on a base surface, d) turning his or her head about 90 degrees and placing the other of said rear posterior surfaces on said base surface, and e) turning his or her head and placing said anterior surface next to said other posterior surface on said base surface.

15. The method of claim 14, comprising the step of vibrating the persons head during at least a part of said process.

16. A method of carrying out a Canalith repositioning maneuver with an apparatus having upper end, a lower end, a front end, a rear end, a cavity formed in said apparatus from said lower end for receiving the head of the person, two outer generally flat posterior surfaces and at least one outer generally flat anterior surface said apparatus having a central plane extending between said front and rear ends, with said anterior surface and one of said posterior surfaces located on one side of said central plane and the other of said posterior surfaces located on the other side of said central plane with said anterior surface and said one posterior surface on opposite sides of said central plane flaring outward and downward relative to each other and said other posterior surface flaring outward and downward, comprising the steps of:

a) placing said apparatus on the head of person such that said front end and rear ends are located at the front and rear of the person's head,
b) with said apparatus on the head of the person, having the person lay down on his or her back,
c) placing one of said posterior surfaces on a base surface,
d) turning his or her head about 90 degrees and placing the other of said posterior surfaces on said base surface, and
e) turning his or her head and placing said anterior surface on said base surface.

17. The method of claim 16, comprising the step of vibrating the persons head during at least a part of said process.

* * * * *